(12) United States Patent
Wanzenboeck et al.

(10) Patent No.: US 8,143,594 B2
(45) Date of Patent: Mar. 27, 2012

(54) METHOD OF DEPOSITING PROTECTIVE STRUCTURES

(76) Inventors: Heinz Wanzenboeck, Vienna (AT); Wolfram Buehler, Hermaringen (DE); Holger Doemer, Bopfingen (DE); Carl Kuebler, Aalen (DE); Daniel Fischer, Dresden (DE); Gottfried Hochleitner, Vienna (AT); Emmerich Bertagnolli, Vienna (AT)

( * ) Notice: Subject to any disclaimer, the term of this patent is extended or adjusted under 35 U.S.C. 154(b) by 141 days.

(21) Appl. No.: 12/658,507

(22) Filed: Feb. 5, 2010

(65) Prior Publication Data

US 2010/0276607 A1  Nov. 4, 2010

(30) Foreign Application Priority Data

Feb. 10, 2009 (DE) .......... 10 2009 008 166

(51) Int. Cl.
  *G01N 1/04* (2006.01)
  *G21K 5/08* (2006.01)
  *C23C 16/48* (2006.01)
(52) U.S. Cl. .......... 250/440.11; 250/311; 427/533; 427/534; 427/585
(58) Field of Classification Search .......... 250/440.11, 250/311; 427/533, 534, 585
  See application file for complete search history.

(56) References Cited

U.S. PATENT DOCUMENTS

| | | | |
|---|---|---|---|
| 5,270,552 A | 12/1993 | Ohnishi et al. | |
| 5,525,806 A | 6/1996 | Iwasaki et al. | |
| 5,800,617 A | 9/1998 | Sandhu | |
| 7,002,152 B2 | 2/2006 | Grunewald | |
| 7,180,061 B2 | 2/2007 | Lu | |
| 7,375,325 B2 * | 5/2008 | Burkhardt et al. | 250/307 |
| 2004/0016880 A1 | 1/2004 | Reiner et al. | |
| 2006/0011868 A1 | 1/2006 | Kidron et al. | |
| 2006/0243919 A1 | 11/2006 | Zhang et al. | |
| 2006/0261270 A1 | 11/2006 | Burkhardt et al. | |
| 2007/0049055 A1 | 3/2007 | Ramaswamy et al. | |
| 2008/0054179 A1 | 3/2008 | Luo et al. | |
| 2010/0300873 A1 * | 12/2010 | Blackwood et al. | 204/192.33 |

FOREIGN PATENT DOCUMENTS

| | | |
|---|---|---|
| EP | 1818970 A2 | 8/2007 |
| WO | 2007051312 A1 | 5/2007 |
| WO | 2008051937 A2 | 5/2008 |
| WO | WO 2008/051880 A2 | 5/2008 |
| WO | WO 2008/051937 A2 | 5/2008 |

OTHER PUBLICATIONS

Office Communication dated Dec. 13, 2010 in European Patent Application 10001225.1-1234 including European Search Report (11 pages).
F. Altmann et al., "TEM preparation by 'low voltage' FIB," Prakt. Metallogr. 43 (2006) 8, pp. 396-405.

(Continued)

*Primary Examiner* — Nikita Wells
(74) *Attorney, Agent, or Firm* — Bruce D Riter

(57) ABSTRACT

A process of preparing a lamella from a substrate includes manufacturing a protection strip on an edge portion of the lamella to be prepared from the substrate, and preparing the lamella, wherein the manufacturing the protection strip includes a first phase of activating a surface area portion of the substrate, and a second phase of electron beam assisted deposition of the protective strip on the activated surface area portion from the gas phase.

19 Claims, 5 Drawing Sheets

OTHER PUBLICATIONS

G. Kerr et al., "Characterisation of electron-beam deposited tungsten interconnects," Electron Microscopy and Analysis Group Conference 2007 (EMAG 2007), Journal of Physics: Conference series 126 (2008) 012073, 4 pages.

H. Wanzenboeck et al., "Perpendicular Iron Nanopillars by Electron Beam Induced Deposition," The Society for Micro- and Nanoelectronics—Biennial Report 2005-2006, pp. 153-157.

H. Mucha et al., "Focused ion beam preparation techniques dedicated for the fabrication of TEM lamellae of fibre-reinforced composites," Journal of Electron Microscopy 51(1): 43-49 (2005).

H. Engelmann, "Advantages and Disadvantages of TEM Sample Preparation Using the FIB Technique," Prakt. Metallogr. 40 (2003) 4, pp. 163-174.

J. Mayer et al., "TEM Sample Preparation and FIB-Induced Damage," MRS Bulletin, vol. 32, May 2007, pp. 400-407.

R. Langford et al., "In situ lift-out: Steps to improve yield and a comparison with other FIB TEM sample preparation techniques," Micron 39 (2008) 1325-1330.

R. Kunz et al., "Catalytic growth rate enhancement of electron beam deposited iron films," Appl. Phys. Lett. vol. 50, No. 15, Apr. 13, 1987, pp. 962-964.

Hiroshi Hiroshima et al: "Conditions for Fabrication of Highly Conductive Wires by Electron-Beam-Induced Deposition", Japanese Journal of Applied Physics, vol. 38, No. Part 1, No. 12B, Dec. 30, 1999, pp. 7135-7139.

Ilya Sychugov et al: "Composition Control of Electron Beam Induced Nanodeposits by Surface Pretreatment and Beam Focusing", Journal of Physical Chemistry C, vol. 113, No. 52, Dec. 31, 2009, pp. 21516-21519.

"Communication pursuant to Article 94(3) EPC" dated Oct. 4, 2011 in European Patent Application No. 10 001 225.1-1234 (English-language document, six pages).

"Result of Consultation" dated Nov. 9, 2011 in European Patent Application No. 10 001 225.1-1234 (English-language document, three pages).

* cited by examiner

METHOD OF DEPOSITING PROTECTIVE STRUCTURES

CROSS-REFERENCES TO RELATED APPLICATIONS

The present application claims priority of German Patent Application No. 10 2009 008 166.6, filed Feb. 10, 2009, the content of which is hereby incorporated by reference in its entirety.

FIELD OF THE INVENTION

The invention relates to a method of depositing protective structures such as e.g. locally confined protective layers on solid substrates, in particular in the course of the preparation of TEM lamellae.

The transmission electron microscopic (TEM) analysis is one of the most powerful analytic methods in semiconductor electronics, at least in part due to its resolution of down to 0.1 nm or less. However, the preparation of suitable TEM samples is complicated, because only ultrathin samples ("lamellae") can be penetrated by the electron beam. The preparation with a focused ion beam (FIB) is particularly suitable, because in this manner, precisely located cross sectional cuts through the sample of interest can be prepared. Herein, two-beam devices with both electron and ion beams are oftentimes used.

BACKGROUND OF THE INVENTION

A method of preparing TEM lamellae is known from international application WO2008/051937 A2. A device for preparing TEM lamellae is disclosed in international application WO2008/051880 A2, the contents of which is hereby incorporated by reference in its entirety. Patent application US 2008/0054179 A1 discloses a method of lamellae preparation employing chemical vapor deposition. Patent application US 2004/0016880 A1 discloses an earlier method of lamellae preparation.

It has been found that in the application of a focused ion beam, scattered, back-scattered and secondary ions present a problem insofar as they lead to amorphisation and gradual erosion of the original sample in particular at the upper edge of the lamella. Furthermore, a contamination with the ions of the beam, e.g. Ga ions, may occur. To prevent his, a local protection strip may be applied to the upper narrow edge of the lamella before beginning with the ion milling to both sides of the protection strip.

To this end, initially a platinum or tungsten strip may be generated via electron beam induced gas phase deposition EBID. The actual protection strip may then be applied onto this strip using ion beam induced gas phase deposition FIB. Depositing the protection strip via FIB without preceding electron beam deposition would lead to the previously mentioned effects, erosion and amorphisation. Following FIB deposition, the substrate is milled on both sides towards the protection strip, leaving only the lamella with the thin protection strip on top. The lamella can then be fastened to a tungsten tip of a nano manipulator via ion beam assisted gas phase deposition, subsequently to be separated at its edges from the substrate and lifted out.

It has now been found that in this procedure, the step of preparing the first layer of the protection strip via electron beam induced gas phase deposition determines the speed of the entire process, because the subsequent ion beam induced deposition is much faster. On the other hand, conventionally, it was not feasible to dispense with this first, slow step, because the direct application of the ion would lead, by erosion or amorphisation, to the destruction of the structures to be inspected.

The present invention has been conceived to overcome the drawbacks of the prior art.

SUMMARY OF THE INVENTION

In embodiments, that portion of the substrate surface where the protective strip is to be applied, is pre-activated and the protective strip is then deposited in that portion.

In embodiments, a significant increase in deposition speed is achieved. Presumably, the pre-activation triggers an auto-catalytic process, as a result of which the electron beam induced deposition proceeds significantly faster, in the case of thermal assistance proceeds at least an order of magnitude faster. Even with thermal assistance, however, and in contrast to known methods without the influence of a particle beam— such as CVD methods—, at moderate temperatures, i.e. temperatures below the decomposition temperature of the precursor, no large-scale deposition occurs, but substantially only deposition in that area covered by the primary electron beam, or in that area affected by secondary effects of the primary electron beam. For example, with moderate heating to 100° C.-150° C., an acceleration by a factor of about 500-1000 can be achieved: Presumably, the influence of the primary electron beam on the substrate leads to a cascade of secondary electrons, which re-emerge from the substrate and induce further deposition reactions.

The amount of acceleration may vary with the type of precursor, substrate material and primary electron energy. A deposition of a first layer of a catalytically active material, or a beam-induced (structural or thermal) pre-activation may be considered as examples for the pre-activation. A thermal pre-activation may be achieved by resistive, conductive and/or radiative heating. The heat source may, in embodiments, be distinct from the electron beam source. The actually achieved surface temperature of the substrate may be detected with suitable means, e.g. IR optically, and may be used to control at least one of the precursor gas supply and the heat source.

Following the accelerated (auto-catalytic) deposition of a layer e.g. 10-30 nm, or up to 200 nm in thickness by means of electron beam induced gas phase deposition, a further e.g. 200-1000 nm may be deposited by means of Ga ion beam induced gas phase deposition, if desired. Equally by means of electron or ion beam induced gas phase deposition, a connection to a nano manipulator may be manufactured; the material deposited in this manner providing a handle to the lamella. The actual preparation of the lamella is performed, in embodiments, by milling with a focused (Ga) ion beam, but without deposition.

By manufacturing the protective strip, in embodiments it is achieved that the preparative ion beam does not lead to electron microscopically detectable lesions of the lamella. To this end, the thickness of the protective strip exceeds the mean penetration depth of the ion beam in the material used for the protective strip, e.g. at least by a factor of two, in embodiments by a factor of 2-5. In other words, the thickness of the strip, expressed in terms of its dependence from its mean mass number $M_S$ and that of the ions of the beam $M_I$, both in u (with u=atomic mass unit), is larger than 7 nm·$[\sqrt{M_I}-2\cdot 1$ g $(M_S/M_C)]$, wherein $M_C$=12 u.

In embodiments, the activating includes the providing of a laterally confined layer, on which the electron beam assisted deposition occurs faster than elsewhere such as in neighboring regions. Namely, the provided layer undergoes a reaction with a gas phase precursor molecule or one adsorbed from the gas phase, the products of which reaction partly remain on the layer and partly desorb. Such exemplary precursor molecules are metal carbonyls, in particular iron, cobalt, chromium or molybdenum carbonyls. In examples, it is suitable to pre-activate the substrate in order to support this process. This may be achieved by heating the substrate to a temperature below that at which spontaneous thermal disintegration of the precursor occurs. For $Fe(CO)_5$, e.g., substrates may be heated to 100° C.-150° C., or in embodiments to 115° C.-130° C.; for $Mo(CO)_6$, temperatures of 200° C.-400° C., or in embodiments of 250° C.-300° C. are suitable. The pressure inside the deposition chamber is e.g. between $10^{-6}$ and $10^{-2}$ mbar, or in embodiments between $10^{-5}$ to $10^{-4}$ mbar. In a case where devices for local gas supply are used, e.g. nozzles or local gas vessels, higher pressures inside the gas vessel are possible, to a maximum of $10^{-2}$ mbar, and lower pressures of down to e.g. $10^{-7}$ mbar outside such vessel or nozzle, respectively. The electron beam energy is set between 0.1 kV and 70 kV, or between 0.5 kV and 50 kV, or suitably between 0.7 kV and 25 kV, or in some embodiments between 1 kV and 10 kV; the beam current is set between 20 pA and 1 µA, or between 200 pA and 50 nA, or in some embodiments between 1 and 5 nA. The layer thickness in some examples is between 10 nm and 2 µm, and in embodiments is between 40 nm and 200 nm, wherein lighter elements may require relatively thicker layers.

In embodiments, the method including a pre-activation results in more atoms being deposited per unit time than without any pre-activation, e.g. at least 1.5 to 50 times as many. When metal carbonyls are used as a precursor, mainly metal atoms and carbon atoms are deposited. In some examples, more metal than carbon, in terms of mass, is deposited, or more metal atoms than carbon atoms. In further embodiments, the initial deposition phase is followed by, firstly, an annealing phase under raised temperature without a reaction gas or electron beam; or secondly, the supply of another reaction gas, which as such does not undergo or support deposition, but benefits the purity or crystallinity of the deposed layer. Furthermore, a precursor may be used which has catalytic or surface-levelling properties.

BRIEF DESCRIPTION OF THE DRAWINGS

The foregoing as well as other advantageous features of the invention will become more apparent from the following detailed description of exemplary embodiments of the invention with reference to the accompanying drawings. It is noted that not all possible embodiments of the present invention necessarily exhibit each and every, or any, of the advantages identified herein.

Figure 1A:
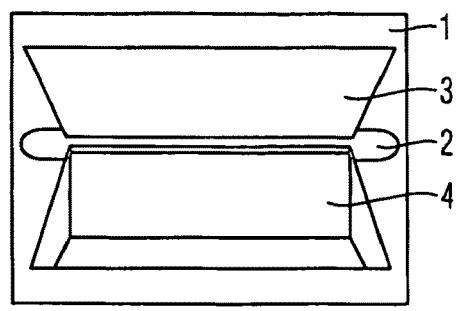
FIGS. 1a,b shows a TEM-lamella with a protective strip deposited according to the invention, in a view tilted to the surface normal.

In the foregoing, those figures indicated by "a" are schematical drawings without any gray levels, and those indicated by "b" are electron microscopic images with gray levels. In the following, these figures will be explained pairwise without any reference to the letters "a" or "b".

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

Figure 1B:
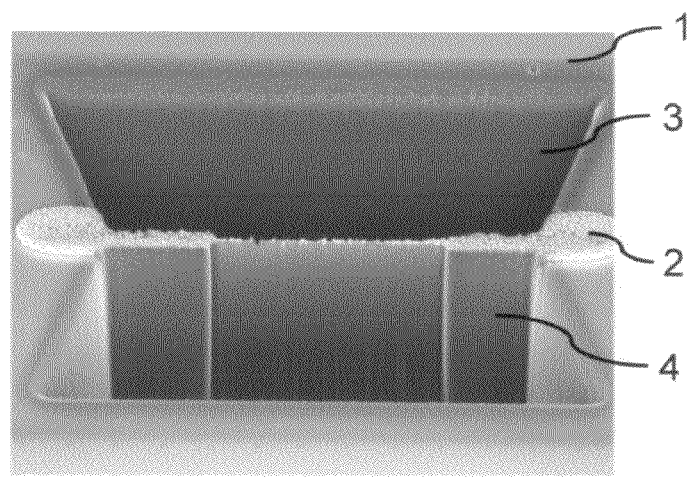

FIG. 1 shows a TEM-lamella 4 with the remainders of a protective strip 2 deposited on its upper edge before preparation of the lamella. This image shows a state, where the substrate material 1 has already been milled out in front of and behind the lamella to form the trough 3, but not yet at its periphery. The thickness of the lamella 4 is suitable set so that there is a reasonable likelihood of finding the material section to be analyzed within it, such as a presumed defect, but on the other hand the analyzing beam can still sufficiently penetrate the lamella 4.

Figure 2A:
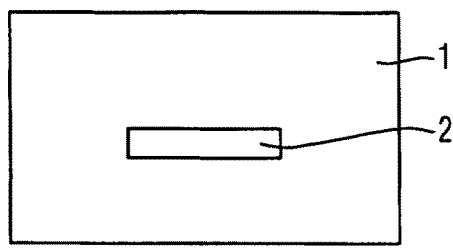
FIGS. 2a,b a deposited protective strip (tilted view)
Figure 3A:
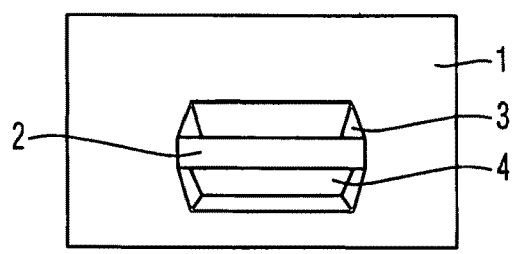
FIGS. 3a,b a lamella prepared by FIB (tilted view)
Figure 4A:
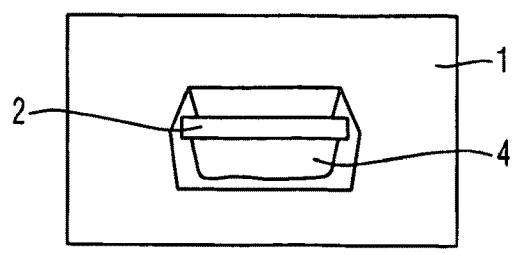
FIGS. 4a,b a lamella almost completely cut out by FIB (tilted view)
Figure 2B:
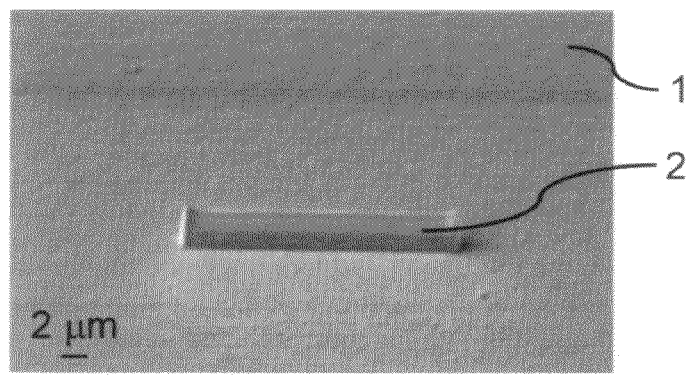
Figure 3B:
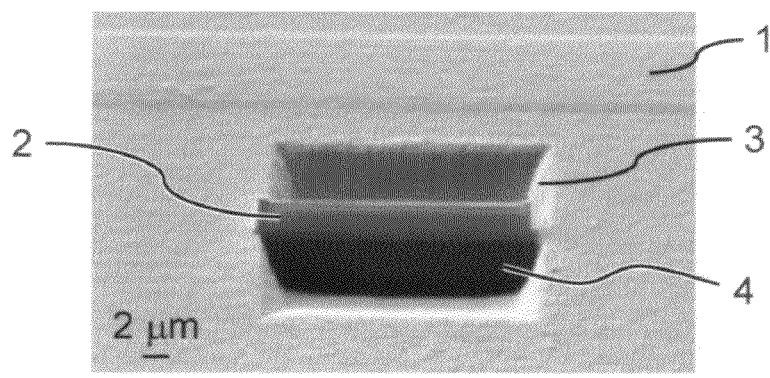
Figure 4B:
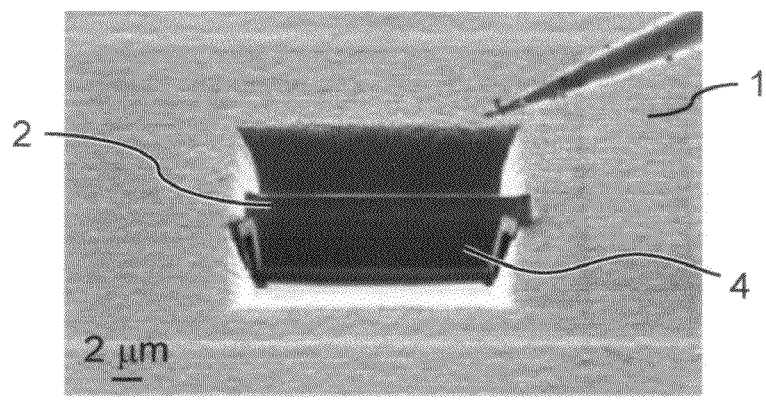
Figure 5B:
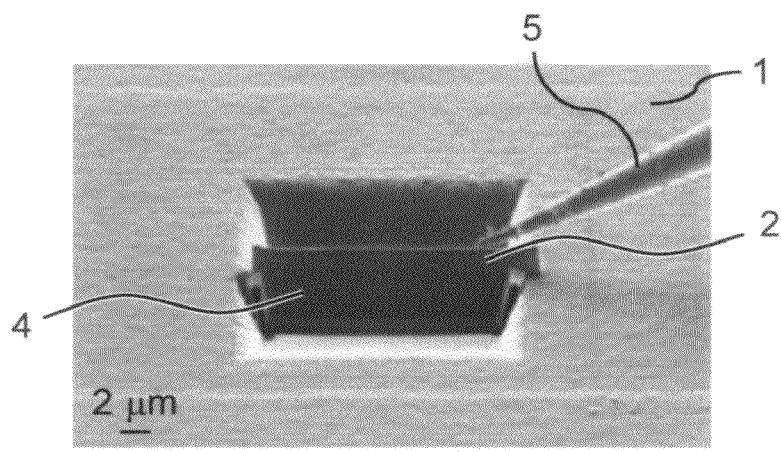
FIGS. 5a,b a lamella with a nano manipulator attached to it (tilted view)

The first step in manufacturing such a TEM-lamella is the deposition of a protective layer 2 in an area at the position of the lamely to be prepared, as shown in FIG. 2, i.e. above the material section to be analyzed, or the presumed defect in the substrate 1, respectively. The manufacturing of this protective strip includes a phase of pre-activating followed by a phase of electron induced gas phase deposition. In embodiments, the activating process ay be continued while the gas phase deposition is going on, such that these steps may be partly simultaneous.

Figure 6B:
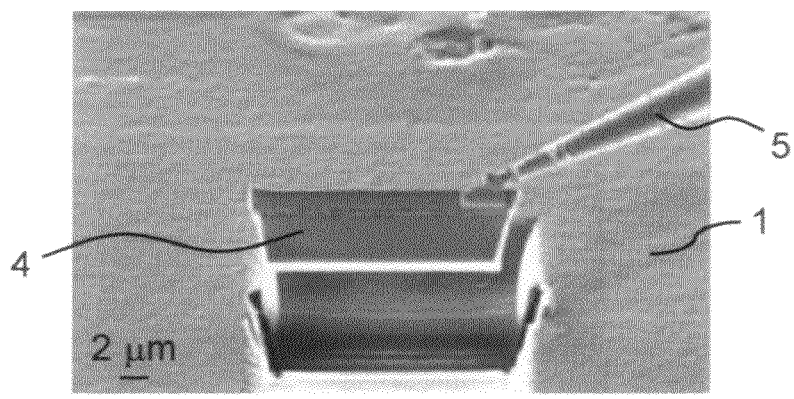
FIGS. 6a,b a lamella lifted out of the substrate (tilted view)
Figure 5A:
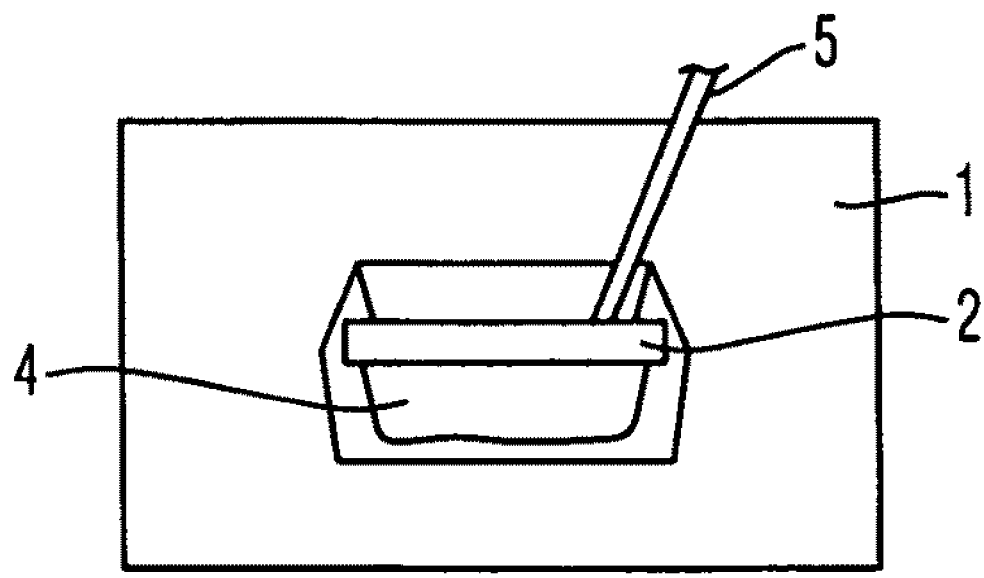
Figure 6A:
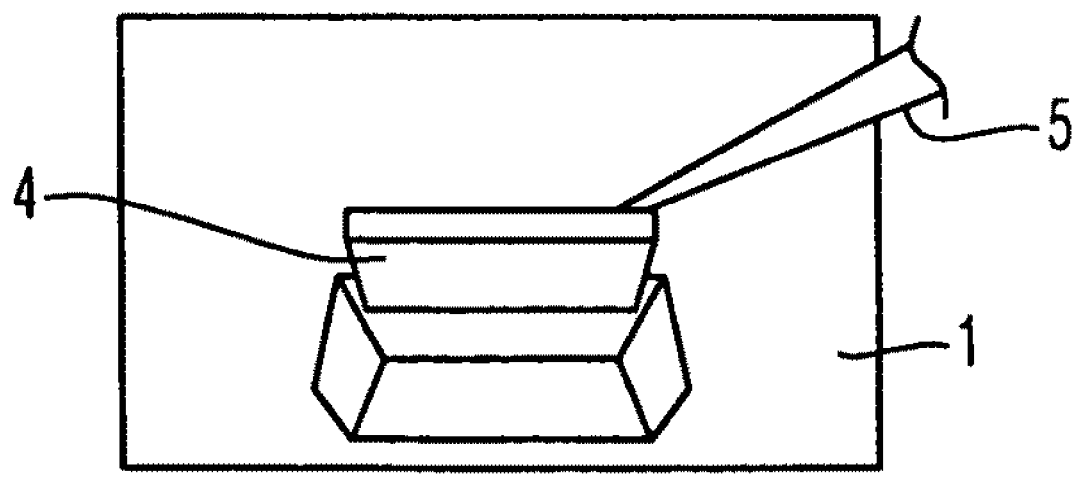

The following steps are shown in FIGS. 3 to 6, namely the preparing the lamella 4 except for its peripheral region (FIG. 3) by hollowing out 3 the substrate 1 on both sides of the lamella, the removing of the main part of the structurally supporting periphery of the lamella 4 (FIG. 4), the attaching of a nano manipulator 5 to the lamella 4 (FIG. 5) and the lifting out of the lamella 4 from the hollowed-out 3 substrate 1 (FIG. 6).

Figure 7:
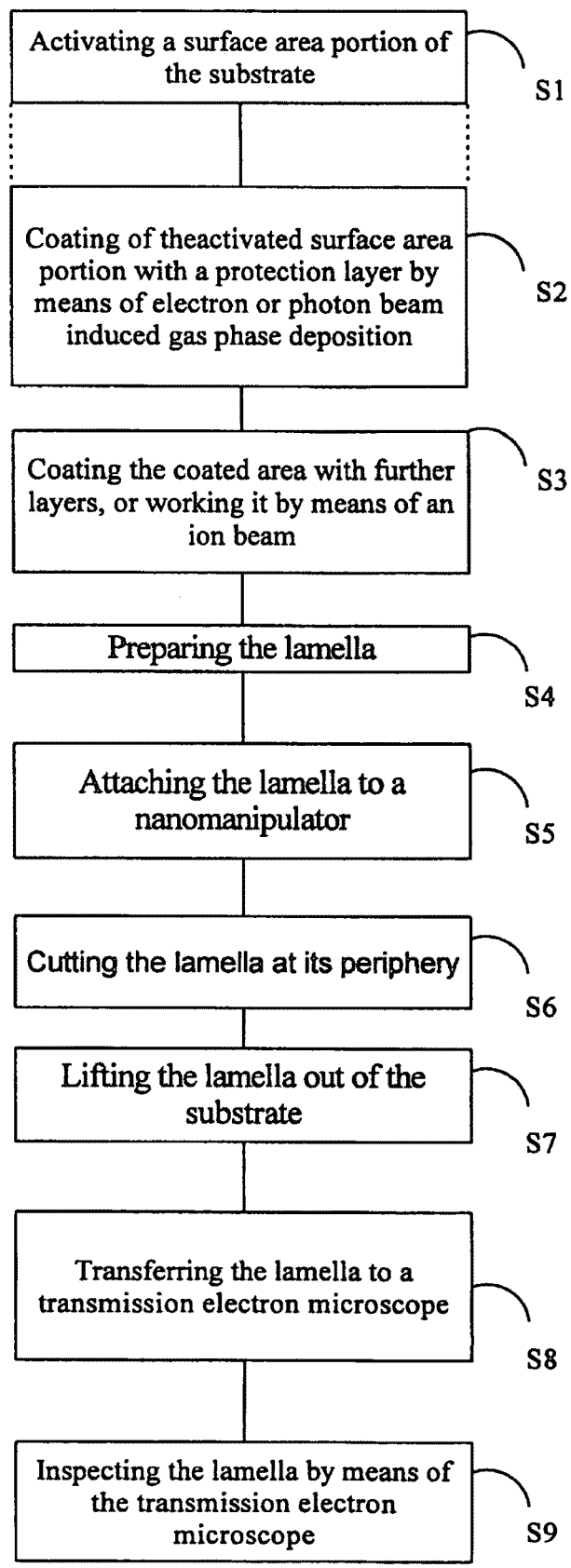
FIG. 7a flow diagram of a method according to the invention.

Finally, in FIG. 7, the manufacturing of the lamella holder is explained by means of a flow diagram: Initially, a surface region of the substrate is activated S1 and, laterally confined, a first protective strip layer is deposited thereon by means of electron beam induced gas phase deposition S2. Herein, the pre-activation and/or the autocatalytic effect is exploited. Steps S1 and S2 may be carried out partly simultaneously, e.g. by continuing the activating process while depositing. Onto the first layer of 10-2000 nm thickness, optionally further layers totaling 100 nm to 1 µm are deposited by means of ion beam induced gas phase deposition S3. Subsequently, the lamella is prepared S4 using a focused ion beam (e.g. a 5-30 keV Ga-beam; or a Helium ion beam). A nano manipulator is attached to the lamella mechanically or by means of ion beam induced deposition, before the lamella is entirely separated from the substrate at its periphery S6. Then, the lamella can be lifted out of the recess in the substrate, or conversely, the substrate can be moved away downwards S7. For inspection, the lamella is transferred S8 to an analyzing device, e.g. into the analyzing beam path of a transmission electron microscope, and there is penetrated by the electron beam and inspected therewith.

The type of the precursor complex and the material to be deposited may be varied as long as a pre-activating or auto-catalytic process is possible. Suitable examples are provided by the carbonyls of Fe, Co, Ni, Mo and W, in particular iron pentacarbonyl $Fe(CO)_5$, dicobalt octa-carbonyl $Co_2(CO)_8$ and molybdenum and tungsten hexacarbonyl Mo(CO)$_6$ and W(CO)$_6$, respectively. More generally, volatile compounds such as organyls or complexes of the transition metal elements of the groups VA to VIIIA, IB or IIB of the periodic system of the elements, in the rows 4 to 6 (except Tc) are suitable. It is also envisaged to deposit several precursor materials simultaneously or subsequently. Further possibilities include the supply of additive gases so as to influence the purity or homogeneity of the deposited layer, or its layer properties. It is further conceivable to reduce the impurity content of the protective layer, in particular its carbon or oxygen content, by a transitory (temporary) elevation of the temperature to e.g. 400° C.-600° C. and/or the addition of reaction gases, before completing the protective layer.

In general, the deposition efficiency is larger than 0.05 atoms/e$^-$ or in some embodiments is larger than 1 atom/e$^-$. In some applications, other organyls, such as dimethyl-platinum (II)-trifluoroacetylacetonate, Pt(AcAc)$_2$ or C-free inorganic complex compounds may be used in place of metal carbonyls. At ambient temperature, or upon moderate warming, e.g. to 120° C., the precursor should be sufficiently volatile, in particular more volatile than the deposited material itself; but should still be sufficiently stable at a somewhat more elevated temperature, so that spontaneous decomposition will not occur during supply. In some examples, the precursor gas is heated to 10°-50° below the decomposition temperature of the precursor, such that same is available in sufficient concentration in the gas phase. In some examples, the substrate is heated to within 10°-50° below the decomposition temperature, such that the precursor gas will not appreciably thermally decompose, or will not deposit spontaneously on the entire surface of the substrate, and on the other hand will remain adsorbed sufficiently long to enable deposition in a significant amount under the influence of the electron beam.

Under such conditions, a precursor can be transported in the gas phase to the site of the lamely to be prepared, and may there initially become adsorbed on the substrate surface, to decompose under the influence of the electron beam accompanied by desorption of the ligand molecules. In some embodiments, the metal layers manufactured making use of pre-activation and/or autocatalysis are relatively poor in carbon and oxygen, as compared to conventionally prepared protective layers. Under these conditions, a deposition with pre-activation, e.g. a thermally assisted electron beam deposition may proceed faster than an ion beam assisted deposition, but avoids damaging the structures of the substrate to be inspected, or its contamination by implantation of primary ions of the beam.

One example of a suitable precursor is iron pentacarbonyl (Fe(CO)$_5$), from which a relatively carbon-poor iron layer may be deposited on a substrate heated to 100° C.-150° C., or in particular to 120° C.-125° C., as compared to conventional EBID without pre-activation. This process is by far faster and more efficient (>100 μm$^3$/μC) than possible with an electron beam at ambient temperature (ca. 0.15 μm$^3$/μC), and is in particular faster than possible with an ion beam.

For comparison, an iron layer was deposited from an iron pentacarbonyl precursor at 1.25·10$^{-5}$ mbar chamber pressure, 20 kV electron energy and 2.07 nA beam current on an area of 10×20 μm$^2$; the obtained thickness was ~4 nm in 40 min. This efficiency of ca. 1.6 μm$^3$/μC would be too low for practical purposes. On the other hand, an iron layer was deposited at again 1.25·10$^{-5}$ mbar chamber pressure, 20 kV electron energy and 2.07 nA beam current, but at 120° C. substrate temperature on an area of 5×25 μm$^2$; the resulting thickness in this case was ~150 nm in 80 sec. This calculates to an efficiency of about 113 μm$^3$/μC, or about 700 times More than at ambient temperature. With this efficiency, a lamella protection layer can be quickly manufactured (without overly delaying the further inspection steps, and) without having to fear damage by ion beams to the substrate structures to be inspected.

Another advantage of some exemplary methods is, at least in some embodiments, the high deposition rate, which in some application renders the application of an ion beam for deposition purposes obsolete. The ion beam would then only be required for the preparation of the lamella itself, or deliberately for planarizing owing to its amorphizing effect.

A further advantage in some embodiments of the inventive metal deposition method is the high purity of the deposited metal, which is beneficial to the conductivity.

In general, the proposed action principle may be applied with suitable precursor gases or reactive gases to other technical fields such as etching processes of for templates for subsequent deposition. E.g., depositions according to the invention or manufactured according to the invention may serve as markers, e.g. for alignment purposes, or as conductive structures, e.g. as a protection against electrostatic charging, or for conductor repair.

In a typical application of the above-described method in the semiconductor industry, a lamella results which is made of a semiconductor substrate, having a metal edge layer, e.g. made of iron, tungsten, molybdenum, gold or platinum. The thickness of the lamella is suitably set so that its absorbing effect on a penetrating analysis electron beam is only as large as tolerable for the remaining intensity of the transmitted electrons to be sufficient for analysis. To this end, a desired limit absorption value may be defined, which is then divided by the electron beam absorption coefficient, in order to obtain the maximally tolerable lamella thickness. In some embodiments, a difference between the base 10 logarithms of the impinging and the minimally transmitted beam intensity is the limit absorption value, which may e.g. be 2 or 1, meaning that at least one hundredth (Lg(100/1)=2) or one tenth (Lg(10/1)=1), respectively, of the impinging power is transmitted.

Because of the avoiding of a Ga ion beam, the lamella in some embodiments is substantially Ga-free in a region directly underneath the protection strip. It is in this region underneath the protection strip, where the areas to be inspected are mostly present in semiconductor substrates. Potential Ga contamination stem from laterally intruding Ga ions during the preparation of the front faces of the lamella. These can, however, be subsequently removed using a low energy Ar ion beam (100-500 eV). In some embodiments, at least no damage due to impinging ions of the beam is discernible. In some embodiments, as an ion source a Be—Si—Au alloy is used, or helium.

The protection layer made according to embodiments from metal carbonyls includes at least 40% metal atoms in addition to mainly carbon and oxygen atoms, or in some embodiments at least 60% metal atoms.

The precursor gas used may have the following properties: On the one hand, the precursor gas dissociates into its components when activated. On the other hand, it may be autocatalytic, meaning that once an initial layer is present, deposited from the precursor gas, the precursor will on its own further dissociate and deposit on the layer or in the vicinity thereof, without or with only little energy supply at slightly elevated temperature or even at ambient temperature, in embodiments between 0° C. and 50° C. As such precursors, metal organyls are suitable, in particular metal carbonyls. The metal carbonyls dissociate in the once activated surface areas—and only there—into metal atoms, splitting off carbon monoxide, and minor or insignificant amounts of carbon and oxygen remaining at the surface. In this manner, a layer is deposited which contains the metal atoms and some carbon and oxygen. As soon as the initial layer is deposited, metal carbonyl molecules adsorbing onto the initial layer continue to dissociate due to the reduced activation energy, so that the layer growth continues on its own, without additional activation by means of an electron beam or another high-energy beam such as an ion beam or light beam being required. However, the further deposition process may in embodiments be supported by the additional application of such a high-energy beam. Alternatively, the area surrounding the desired deposition area may be optically activated in such a manner that adsorption in this area is suppressed, and occurs only in the non-illuminated area. In this manner, it can be achieved that deposition only or predominantly occurs in the desired area.

Without wishing to be bound by theory, the precursor gas may have the property of the presence of components of already dissociated molecules leading to a reduction of the activation energy required for dissociation. The deposited layer thus includes a first layer directly deposited on the surface of the substrate from such a precursor gas.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A process of preparing a lamella from a substrate, the process comprising:
    manufacturing a protection strip on an edge portion of the lamella to be prepared from the substrate; and
    preparing the lamella,
wherein the manufacturing the protection strip comprises a first phase of activating a surface area portion of the substrate, and a second phase of particle beam assisted deposition of the protective strip on the activated surface area portion from the gas phase.

2. The process of claim 1, wherein in the second phase, the deposition occurs from a precursor gas, which gas dissociates in the surface area portion activated in the first phase, and does not dissociate in a portion not activated in the first phase.

3. The process of claim 1, wherein the first phase and the second phase are made to occur simultaneously, alternatingly or with a waiting interval in between.

4. The process of claim 1, wherein the lamella is prepared using an ion beam.

5. The process of claim 4, wherein the ion beam is a focussed ion beam (FIB).

6. The process of claim 4, wherein the ion beam is a Ga ion beam.

7. The process of claim 4, wherein the preparing is made by ion beam milling.

8. The process of claim 4, wherein the protection strip is manufactured in a thickness and from a material, such that the preparation ion beam electron causes no microscopically detectable damage to the edge portion of the lamella.

9. The process of claim 4, wherein the thickness of the protective strip is made larger than a mean penetration depth of the preparation ion beam in the material of the protection strip.

10. The process of claim 9, wherein the thickness of the protective strip is made at least 1.5 times as large as the mean penetration depth of the preparation ion beam in the material of the protection strip.

11. The process of claim 4, wherein the thickness of the protective strip is selected at least twice as large as the mean penetration depth of the preparation ion beam in the material of the protection strip.

12. The process of claim 1, wherein the activating is at least partially thermal.

13. The process of claim 12, wherein no ion beam is used in the deposition.

14. The process of claim 1, wherein the protection strip is manufactured using at least one of iron, cobalt, chromium, molybdenum, tungsten, gold and platinum.

15. A lamella for TEM-analysis, comprising:
    a plate made of a substrate material, wherein the thickness of the plate is smaller than a first limit value, at which a difference of the base 10 logarithms of the incident analysis electron beam intensity and the minimally transmitted analysis electron beam intensity is 2; and by
    a layer arranged at an edge portion of the plate, the layer consisting essentially of a metal, carbon and oxygen.

16. The lamella of claim 15, wherein the edge layer comprises less carbon, by mass, than metal.

17. The lamella of claim 15, wherein the edge layer comprises at least 40% metal atoms.

18. The lamella of claim 17, wherein the edge layer comprises at least 60% metal atoms.

19. The lamella of claims 15, wherein the thickness of the lamella is smaller than a second limit value, at which a difference of the base 10 logarithms of the incident analysis electron beam intensity and the minimally transmitted analysis electron beam intensity is 1.

* * * * *

UNITED STATES PATENT AND TRADEMARK OFFICE
CERTIFICATE OF CORRECTION

PATENT NO. : 8,143,594 B2
APPLICATION NO. : 12/658507
DATED : March 27, 2012
INVENTOR(S) : Heinz Wanzenboeck et al.

It is certified that error appears in the above-identified patent and that said Letters Patent is hereby corrected as shown below:

Column 2, lines 53-63 should read:

By manufacturing the protective strip, in embodiments it is achieved that the preparative ion beam does not lead to electron microscopically detectable lesions of the lamella. To this end, the thickness of the protective strip exceeds the mean penetration depth of the ion beam in the material used for the protective strip, e.g. at least by a factor of two, in embodiments by a factor of 2-5. In other words, the thickness of the strip, expressed in terms of its dependence from its mean mass number $M_S$ and that of the ions of the beam $M_I$, both in u (with u = atomic mass unit), is larger than $$7\ nm \cdot [\sqrt{M_I} - 2 \cdot lg(M_S/M_C)],$$

wherein $M_C$ = 12 u.

Signed and Sealed this
Twenty-sixth Day of June, 2012

David J. Kappos
*Director of the United States Patent and Trademark Office*